United States Patent [19]

Yan

[11] Patent Number: 5,004,854
[45] Date of Patent: Apr. 2, 1991

[54] PSEUDOCUMENE AND MESITYLENE PRODUCTION AND COPRODUCTION THEREOF WITH XYLENE

[75] Inventor: Tsoung Y. Yan, Philadelphia, Pa.

[73] Assignee: Mobil Oil Corp., Fairfax, Va.

[21] Appl. No.: 937,845

[22] Filed: Dec. 4, 1986

[51] Int. Cl.$^5$ .............................................. C07C 4/12
[52] U.S. Cl. ..................................... 585/489; 585/486
[58] Field of Search ..................... 585/475, 486, 489

[56] References Cited

U.S. PATENT DOCUMENTS

| | | | |
|---|---|---|---|
| 2,385,524 | 9/1945 | Mattox | 585/474 |
| 2,564,388 | 8/1951 | Bennett et al. | 585/479 |
| 3,168,583 | 2/1965 | Kouach | 585/489 |
| 3,646,236 | 2/1972 | Keith et al. | 585/474 |
| 3,691,247 | 9/1972 | Billings | 585/481 |
| 3,945,913 | 3/1976 | Brennan et al. | 208/137 |
| 4,188,282 | 2/1980 | Tabak et al. | 208/134 |
| 4,236,996 | 12/1980 | Tabak et al. | 585/489 |
| 4,320,242 | 3/1982 | Onoders et al. | 585/489 |
| 4,469,909 | 9/1984 | Chester et al. | 585/481 |
| 4,577,050 | 3/1986 | Kaeding et al. | 585/486 |
| 4,593,136 | 6/1986 | Kaeding et al. | 585/446 |
| 4,626,609 | 12/1986 | Shihabi | 585/467 |
| 4,665,255 | 5/1987 | Chang et al. | 585/467 |

*Primary Examiner*—Curtis R. Davis
*Attorney, Agent, or Firm*—Alexander J. McKillop; Charles J. Speciale; Edward F. Kenehan, Jr.

[57] ABSTRACT

A process for the production of pseudocumene, mesitylene, xylenes and benzene by upgrading $C_9$ aromatics or mixtures of $C_7$–$C_9$ aromatics is disclosed. The process is carried out under catalytic upgrading conditions using a catalyst which comprises a crystalline zeolite having a silica-to-alumina ratio of at least about 12 and a constraint index from about 1 to about 12, the zeolite preferably being ZSM-5.

15 Claims, 1 Drawing Sheet

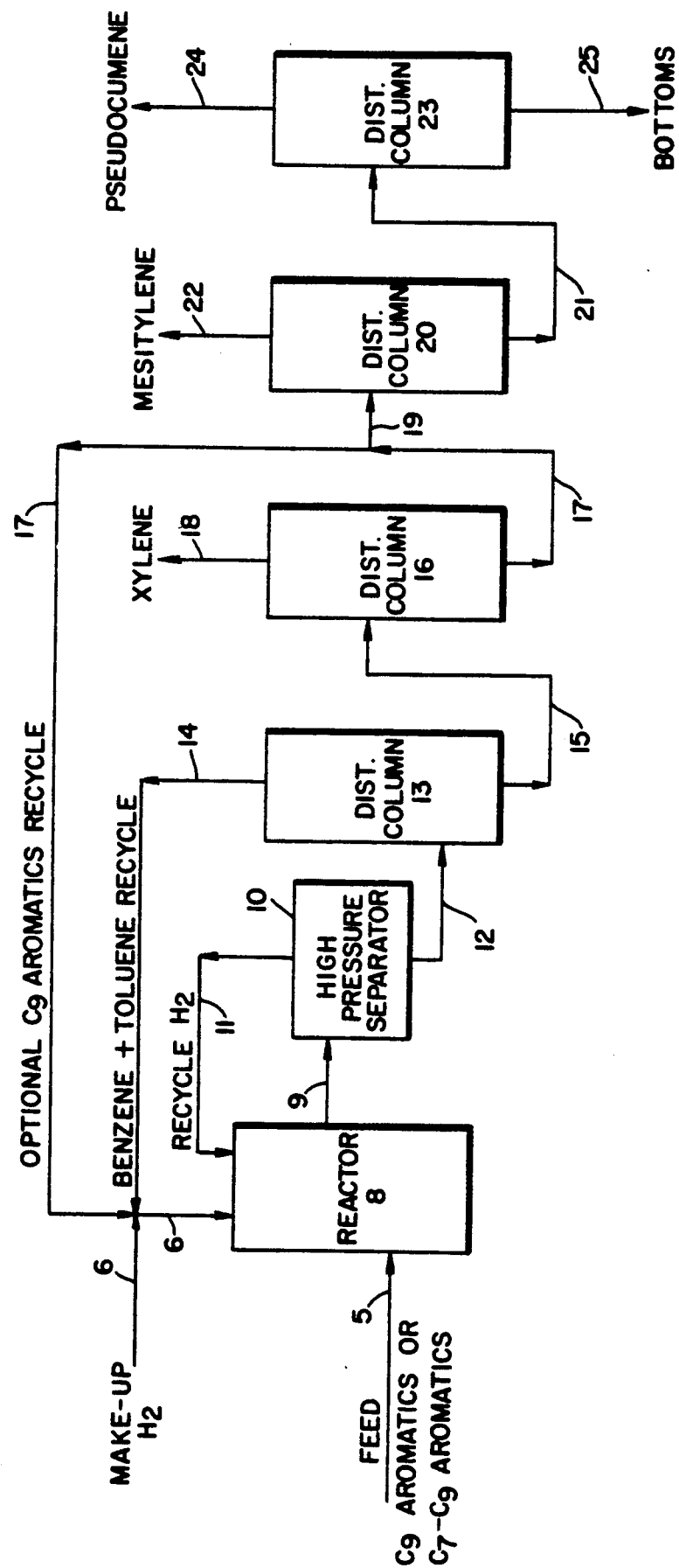

PSEUDOCUMENE AND MESITYLENE PRODUCTION AND COPRODUCTION THEREOF WITH XYLENE

BACKGROUND OF THE INVENTION

1. Field of the Invention

This invention relates to the upgrading of $C_9$ aromatics to produce pseudocumene, mesitylene, xylenes, and benzene over shape-selective zeolite catalysts having a silica-to-alumina ratio of at least about 12 and a constraint index from about 1 to about 12.

2. Description of Related Art

Xylenes and higher aromatics such as pseudocumene and mesitylene are desired commercial products having various uses as disclosed in N. E. Ockerbloom's article, "Xylenes and Higher Aromatics" in *Hydrocarbon Processing*, April 1972, pg. 114–118. This article discloses that these products can be obtained through fractional distillation or extraction from $C_9$ aromatic fractions obtained from naphtha cracking or reformate.

Catalytic cracking, reforming, disproportionation, and isomerization of higher hydrocarbons is also well known in the prior art. For example, U.S. Pat. Nos. 4,163,028, 4,218,573, and 4,236,996, all issued to Tabak et al, and U.S. Pat. No. 4,159,282, issued to Olson et al, disclose the isomerization of xylene contained in a $C_8$ aromatics feedstock in the presence of a ZSM-5 or related zeolite catalyst. U.S. Pat. No. 4,313,021, issued to Ryu, discloses reactions such as alkylation, transalkylation of ethylbenzene and the isomerization of m-xylene in the presence of an alumina-titanium fluoride catalyst. U.S. Pat. No. 4,260,843, issued to Chu, discloses alkylation of toluene and the disproportionation of toluene in the presence of ZSM-5. The ZSM-5 can be modified by the addition of phosphorus or beryllium. U.S. Pat. No. 4,454,364, issued to Farcasiu et al discloses acid-catalyzed transalkylation among benzenoid species. U.S. Pat. No. 4,127,471, issued to Suggitt et al, discloses the hydrocracking of alkylaromatic hydrocarbons, and then transferring alkyl groups from one alkylaromatic product to the other in the presence of a solid alkyl transfer catalyst with a silica-to-alumina ratio about about 12:1. U.S. Pat. No. 4,418,235, issued to Haag et al, discloses hydrocarbon conversion processes such as cracking, hydrocracking, alkylation, dealkylation, transalkylation, isomerization, dimerization, oligomerization, disproportionation, aromatization, and hydration with a zeolite catalyst having an enhanced alpha activity. The zeolite is selected from the group consisting of ZSM-5, ZSM-11, ZSM-12, ZSM-23, ZSM-35, and ZSM-38. U.S. Pat. No. 4,041,091 deals with a fractionation process whereby a mixture of toluene and $C_9$ aromatics is converted to benzene and $C_8$ aromatics. A similar process is also disclosed in U.S. Pat. No. 3,996,305, issued to Berger. U.S. Pat. No. 3,784,621, issued to Suggitt, discloses a process whereby toluene is contacted with a disproportionation catalyst, a $C_8$ aromatic fraction is then separated, and this $C_8$ aromatic fraction is contacted with a disproportionation catalyst in order to form a $C_9$ aromatic fraction. The $C_9$ aromatic fraction may contain pseudocumene and/or mesitylene. U.S. Pat. No. 4,117,026, issued to Haag et al, discloses the production of para-dialkyl-substituted benzenes. The alkyl groups each contain from 1 to 4 carbon atoms. The process uses a zeolite catalyst with a silica-to-alumina ratio of at least about 12 and has a constraint index from about 1 to about 12.

SUMMARY OF THE INVENTION

In accordance with the present invention, it has been discovered that $C_9$ alkylaromatics can be upgraded to high concentrations of valuable trimethylbenzenes by the use of certain shape-selective catalysts which convert propyl and methylethylbenzenes, the labile $C_9$ aromatics, to xylene and benzene without converting trimethylbenzenes such as pseudocumene and mesitylene. By means of the invention, less valuable $C_9$ aromatic streams are upgraded to more valuable aromatics such as pseudocumene, mesitylene, xylene and benzene. The invention offers the advantage of simplicity since the $C_9$ feedstock may be processed in conventional disproportionation apparatus by changing the feed material and installing two additional distillation columns for recovery of pseudocumene and mesitylene. Additionally, the $C_9$ aromatic feed stream, if desired, may be coprocessed with toluene or $C_7$ to $C_9$ mixed aromatic feedstocks to provide increased xylene yields while also producing pseudocumene and mesitylene.

BRIEF DESCRIPTION OF THE DRAWING

The embodiment of the invention illustrated in the drawing shows an upgrading reactor and the various distillation columns which are interconnected to recover benzene, xylenes, pseudocumenes and mesitylene.

DESCRIPTION OF PREFERRED EMBODIMENTS

In accordance with the drawing, a reactant stream comprising $C_9$ alkylaromatics is introduced into reactor 8 via line 5, hydrogen is added through line 6 and both materials are contacted therein with a shape-selective zeolite catalyst more fully described hereinafter. A principal source of the $C_9$ aromatic feed stream may be found in catalytically reformed naphthas in which a $C_9$ heart cut or extract of the reformate is enriched in $C_9$ alkylbenzenes, a typical reformate containing as much as 57% trimethylbenzenes based on the total content of $C_9$ aromatics. The composition of a $C_9$ heart cut is typically about 2.5, 87.5 and 10 mole % of $C_8$, $C_9$ and $C_{10}$ aromatics, respectively. Other sources of $C_9$ aromatic feedstocks are derived from gasoline producing processes such as the conversion of methanol to gasoline, as described in U.S. Pat. Nos. 3,931,349, 3,969,426, 3,899,544, 3,894,104, 3,904,916 and 3,894,102, and the conversion of synthesis gas to gasoline as described in U.S. Pat. Nos. 4,096,163, 4,279,830, 4,304,871 and 3,254,023, all of which are incorporated by reference. A $C_7$–$C_9$ mixed aromatic feedstock also may be used and can be derived from various sources including petroleum refinery sources, pyrolysis of coal to produce coke, tar sands, etc. In petroleum processing operations such as transalkylation, isomerization and disproportionation, for example, the product streams so produced are further treated, by fractionation, etc., to obtain alkylaromatic streams which contain substantial quantities of alkylbenzenes such as toluene, xylenes, and trimethylbenzenes. A typical alkylaromatic fraction which may be obtained contains predominantly $C_7$ to $C_9$ hydrocarbons and is referred to as crude xylenes. In the present illustration, a $C_7$–$C_9$ feedstock is introduced via line 5 to reactor 8 at the rate of 20,900 pounds per hour together with recycle toluene from distillation column 13 via lines 14 and 6. The feedstock is also admixed with 200 moles/hour of a hydrogen gas introduced from line 6 and 3870 pounds per hour of $C_9$ aromatics recycle from line 17. Upgrading of the charge stream is carried out over a catalyst such as ZSM-5 in the vapor phase at temperatures of 700° to 1100° F., preferably about 800° to 1000° F., pressures of 15 to 2000 p.s.i.g., preferably 150 to 800 p.s.i.g., weight hourly space velocities of 0.2 to 10, preferably 1.0 to 5.0, and hydrogen to hydrocarbon mole ratios of 0.5 to 10, preferably about 1 to 5. Reactor 8 contains heating, pumping, recycle gas compression and separation means, etc., all known in the art. The resultant effluent from reactor 8, analyzed and summarized in Table 1, is passed via line 9 to high pressure separator 10 where a hydrogen recycle stream of 180 moles/hour is withdrawn via line 11 for recycle to reactor 8. Although the formation of light gases occurs in small amounts in reactor 8, the hydrogen is substantially pure for purposes of recycle. In some instances it may be desirable, however, to further purify the hydrogen stream before recycling it to the reactor. The product effluent from separator 10 is passed through line 12 into first distillation column 13 and a first overhead fraction including 25230 pds/hour toluene is removed from column 13 and recycled to reactor 8 via lines 14 and 6. The bottoms fraction from column 13 comprising $C_8$, $C_9$ and $C_{10}$ aromatics is sent to second distillation column 16 via line 15 where 11,000 lbs/hr of the xylene fraction is recovered via line 18. This fraction will also contain a small amount, e.g., 1.4 wt.%, of ethylaromatic hydrocarbons such as ethylbenzene. Individual isomer products may be separated by appropriate physical methods, e.g., fractional crystallization. $C_9$ alkylbenzenes such as propylbenzene, methylethylbenzene and trimethylbenzene, and the $C_{10}$ heavier aromatics are removed through line 17 and may be recycled to reactor 8 to maximize xylene yields or sent to third distillation column 20 via line 19.

For mesitylene and pseudocumene production, the $C_9$ aromatics are not recycled and the bottoms fraction introduced to distillation column 20 via line 19 includes the $C_9$ and $C_{10}$ aromatic fractions. As illustrated, mesitylene is separated by distillation as an overhead product and is withdrawn from column 20 at a rate of 681 lbs/hour via line 22. The bottoms fraction, which includes the $C_9$ pseudocumene and $C_{10}$ fraction is passed into fourth distillation column 23 via line 21 where pseudocumene is distilled and recovered as an overhead product in line 24 at a rate of 3092 lbs/hour. The $C_{10}+$ bottoms fraction is withdrawn via line 25 and may be recycled to reactor 8 or routed to a motor naphtha pool.

TABLE I

| FEED, LBS/HR Component | FRESH FEED | $C_9$ AROMATICS RECYCLE | TOLUENE RECYCLE | TOTAL CHARGE | TOTAL EFFLUENT |
|---|---|---|---|---|---|
| C2 to C5 | | | | | 2200 |
| Benzene | | | | | 7300 |
| Toluene | 13585 | | 25230 | 38815 | 25230 |
| Ethylbenzene | | | | | 150 |
| Xylenes | | | | | 11000 |
| Propylbenzene | 585 | 40 | | 625 | 40 |
| N-nonane | 365 | | | 365 | |
| Methyl-ethylbenzene | 2305 | 120 | | 2425 | 120 |
| Trimethylbenzene | 4025 | 3710 | | 7735 | 3710 |
| Indane | 35 | | | 35 | |
| Butylbenzene | | | | | 250 |
| TOTAL | 20900 | 3870 | 25230 | 50000 | 50000 |

The reactants suitable for the present process are $C_9$ alkylaromatics or a $C_7$ to $C_9$ mixture of alkylaromatics. The $C_9$ alkylaromatic hydrocarbons are characterized as mainly monocyclic aromatic compounds, such as alkylbenzenes, which have at least one transferable alkyl group which preferably contains no more than 4 carbon atoms. The $C_9$ aromatic hydrocarbons include, for example, 1,2,3 trimethylbenzene (hemimellitene), 1,2,4 trimethylbenzene (pseudocumene), 1,3,5 trimethylbenzene (mesitylene), isopropylbenzene (cumene), 1,2 methylethylbenzene, 1,3 methylethylbenzene, and 1,4 methylethylbenzene. As mentioned above, the $C_9$ aromatics for use in the present process are conveniently available as product streams from various petroleum processing operations including gasoline producing processes such as the conversion of methanol to gasoline or the conversion of carbon monoxide and hydrogen (syngas) to gasoline. Catalytic reformates, for example, are particularly preferred since they are enriched in aromatics and the $C_9$ fraction can be readily separated from non-aromatics by extraction with aqueous glycols, typically a Udex unit. The typical composition of extracted $C_9$ reformate and the boiling points of the $C_9$ aromatics contained therein are shown below in Table II.

TABLE II

COMPOSITION OF $C_9$ AROMATICS IN EXTRACTED REFORMATE

| Compound | Boiling Point (°F.) | Freezing Point (°F.) | Wt. % (based on total $C_9$ aromatics) |
|---|---|---|---|
| API Gravity | — | | |
| IBP, °F. | — | | |
| EBP, °F. | — | | |
| Isopropylbenzene | 306 | −141 | 0.6 |
| n-Propylbenzene | 319 | −147 | 5.2 |
| m-Ethyltoluene | 322 | −140 | 17.4 |
| p-Ethyltoluene | 324 | −80 | 8.6 |
| 1,3,5-Trimethylbenzene (mesitylene) | 329 | −49 | 7.6 |
| o-Ethyltoluene | 329 | −114 | 9.1 |
| 1,2,4-Trimethylbenzene (pseudocumene) | 337 | −47 | 41.3 |
| 1,2,3-Trimethylbenzene (hemimellitene) | 349 | −14 | 8.2 |
| Indane | 352 | — | 2.0 |
| | | | 100.0% |

While the quality of crudes may affect the quantity and type of $C_9$ aromatics extracted from a naptha reformate, about 57 wt. % of the total $C_9$ aromatics are trimethylbenzenes in which pseudocumene, mesitylene and hemimellitene are typically produced in the following ratios:

| | |
|---|---|
| Pseudocumene | = 1 |
| Mesitylene | = 0.18 |
| Hemimellitene | = 0.20 |

The $C_9$ aromatics may be further characterized as having an initial boiling point range of 230°–280° F., an end boiling point range of 350°–425° F., and an API gravity of 35–60.

In the practice of the invention, a C9 alkylaromatic charge stream having the approximate composition shown in Table II is charged to reactor 8 and upgraded to pseudocumene, mesitylene, xylenes, and benzene over a shape-selective zeolite catalyst having a silica-to-alumina ratio of 1 to 12. An essential aspect of the invention is the use of a shape-selective catalyst for upgrading whereby labile $C_9$ aromatics, such as propyl and methylethylbenzenes are selectively converted to xylene, toluene, benzene and small amounts of light gases without converting the trimethylbenzenes.

Since relative rate constants for the conversion of labile $C_9$ aromatics and trimethylbenzenes are 5:1 to 20:1, it is thus possible to convert propyl and methylethylbenzenes, the labile $C_9$ aromatics, to xylene, benzene and small amounts of light gases by dealkylation, disproportionation and transalkylation without converting pseudocumene or mesitylene. The shape selectivity characteristic of the catalyst concentrates the trimethylbenzenes and offers the further advantage of selectively cracking small amounts of paraffins and naphthenes in the feed to reduce the formation of dicyclic aromatics, durene and coke precursor materials. Selective conversion of paraffins also makes the recovery and purification of trimethylbenzenes, particularly pseudocumene, possible using a rather simple distillation. During the upgrading process, the hydrocarbons undergo a combination of reactions including cracking, alkylation, dealkylation, isomerization, transalkylation and disproportionation. It has been discovered that a shape-selective catalyst such as HZSM-5 selectively forms pseudocumene leading to increased yield and purity.

In the practice of another aspect of the invention, the charge introduced by line 5 is primarily a mixture of seven to nine carbon atom alkyl aromatics which include $C_7$ and $C_8$ aromatics, such as toluene, ethylbenzene and xylenes, and the $C_9$ alkyl aromatic identified in Table II above. Such charge stocks may also be derived from catalytic reformates, pyrolysis gasoline, etc., by distillation and solvent extraction to separate aromatic compounds from aliphatics. Other sources of suitable charge stocks include crude xylene streams, which actually contain alkylaromatics having 7 to 9 carbon atoms, and effluents from toluene transalkylation reaction zones which contain benzene, xylene, $C_9$ aromatics, and aromatics heavier than $C_9$. Mixtures of toluene and $C_9$ alkylaromatics may also be employed. In this aspect of the invention, two moles of a single aromatic, such as toluene, are upgraded by disproportionation to one mole each of two different aromatics, xylenes and benzene. Transalkylation also occurs and one or two moles each of two different aromatics, e.g., methylethylbenzene or propylbenzene, will react with one mole of toluene or benzene to produce xylenes. Thus, direct transalkylation of the labile $C_9$ aromatics contribute significantly to increased yields of xylenes. Additionally, positional isomerization of polyalkylbenzenes also occurs via intramolecular shift and increased yields of mesitylene may be obtained from pseudocumene. The composition of a typical $C_7$–$C_9$ reformate cut is shown below in Table III.

TABLE III

| Products: | Analysis wt. percent |
|---|---|
| Naphthenes | 0.15 |
| Benzene | 2.03 |
| Toluene | 19.69 |
| Ethylbenzene | 0.004 |
| Paraxylene | 12.04 |
| Metaxylene | 27.64 |
| Orthoxylene | 10.40 |
| p-Ethyltoluene | 0.02 |
| m-Ethyltoluene | 0.06 |
| o-Ethyltoluene | 0.01 |
| Mesitylene | 7.18 |
| Pseudocumene | 15.82 |
| Hemimellitene | 1.93 |
| Ethylxylenes | 0.13 |
| Durene | 1.19 |
| Isodurene | 1.43 |
| Prehnitene | 0.28 |

The $C_7$ to $C_9$ aromatic mixture may be further characterized as having an initial boiling point range of 150° F., an end boiling point range of 350° F., and an API gravity of about 40.

The shape-selective zeolite catalysts used for purposes of upgrading in this invention are characterized by a framework silica-to-alumina ratio of at least about 12 and a Constraint Index of from about 1 to about 12. Non-limiting members of ths class of zeolites include ZSM-5, ZSM-11, ZSM-12, ZSM-22, ZSM-23, ZSM-35, ZSM-38, ZSM-48, ZSM-50 and other similar materials. The preferred crystalline zeolites are ZSM-5, ZSM-11, ZSM-12, ZSM-23, ZSM-35 and ZSM-38, with ZSM-5 being particularly preferred.

ZSM-5 is described in greater detail in U.S. Pat. No. 3,702,886, the entire contents of which are incorporated herein by reference.

ZSM-11 is described in U.S. Pat. No. 3,709,979, the entire contents of which are incorporated herein by reference.

ZSM-12 is described in U.S. Pat. No. 3,832,449, the entire contents of which are incorporated herein by reference.

ZSM-22 is described in U.S. Pat. No. 4,481,177, the entire contents of which are incorporated herein by reference.

ZSM-23 is described in U.S. Pat. No. 4,076,842, the entire contents of which are incorporated herein by reference.

ZSM-35 is described in U.S. Pat. No. 4,016,245, the entire contents of which are incorporated herein by reference.

ZSM-38 is described in U.S. Pat. No. 4,046,859, the entire contents of which are incorporated herein by reference.

ZSM-48 is described in U.S. Pat. No. 4,375,573, the entire contents of which are incorporated herein by reference.

ZSM-50 is described in U.S. application Ser. No. 719,611, filed Apr. 3, 1985, which is a division of U.S. application Ser. No. 386,456, filed June 8, 1982, now abandoned, the entire contents of which are incorporated herein by reference.

It is to be understood that by incorporating by reference the foregoing patents to describe examples of specific members of the class of shape-selective zeolites contemplated, it is intended that identification of the disclosed crystalline zeolite be resolved on the basis of their respective X-ray diffraction patterns. Thus, the present invention contemplates utilization of such catalysts wherein the mole ratio of silica to alumina is essentially unbounded. The incorporation of the identified patents should therefore not be construed as limiting the disclosed crystalline zeolites to those having the specific silica-alumina mole ratios discussed therein, it now being known that such zeolites may be substantially aluminum-free and, yet, have the same crystal structure as the disclosed materials and may be useful or even preferred in some applications. It is the crystal structure, as identified by the X-ray diffraction "fingerprint" which establishes the identity of the specific crystalline zeolite material.

In practicing the upgrading conversion process, it may be desirable to incorporate the above-described crystalline zeolite with a matrix comprising another material resistant to the temperature and other conditions employed in the process. Such matrix material is useful as a binder and imparts greater resistance to the catalyst for the sever temperature, pressure and reactant feed stream velocity conditions encountered in many cracking processes.

Useful matrix materials are well known and include both synthetic and naturally occurring substances, as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The matrix, on an anhydrous basis, may vary widely with the zeolite content ranging from between about 1 to about 99 percent by weight and more usually in the range of about 5 to about 80 percent by weight of the dry composite.

The catalyst composition preferably contains a hydrogenating component which is usually derived from a metal of Groups VIA or VIIIA of the Periodic Table. (The Periodic Table used in this specification is the table approved by IUPAC and the United States National Bureau of Standards and is known, for example, as the Table of the Fisher Scientific Company, Catalog No. 5-702-10.) Preferred non-noble metals are tungsten, molybdenum, nickel, cobalt, and chromium, and the preferred noble metals are platinum, palladium, iridium and thodium. Combinations of non-noble metals selected from nickel, cobalt, molybdenum and tungsten are exceptionally useful with many feedstocks. The amount of hydrogenation component that may be employed is not narrowly critical and can vary from about 0.01 to about 5.0 weight percent based on the total catalyst. It is to be understood that the non-noble metal combinations may be in the oxide or sulfide form. The hydrogenation component can be exchanged into the zeolite, impregnated or physically admixed with the zeolite. If the metal is to be impregnated onto or exchanged into the zeolite, it may be done, for example, by treating the zeolite with a platinum metal-containing ion. Suitable platinum compounds include chloroplatinic acid, platinous chloride and various compounds containing the platinum ammine complex. The hydrogenation component can also be present in matrix material used to bind the zeolite components.

The catalyst may be treated by conventional pre-sulfiding treatments, e.g., by heating in the presence of hydrogen sulfide, to convert oxide forms of the metals such as CoO or NiO to their corresponding sulfides.

The metal compounds may be either compounds in which the metal is present in the cation of the compound or compounds in which it is present in the anion of the compound. Both types of compounds can be used. Platinum compounds in which the metal is in the form of a cation or cationic complex, e.g., $Pt(NH_3)_4Cl_2$ are particularly useful, as are anionic complexes such as the metatungstate ions. Cationic forms of other metals are also very useful since they may be exchanged onto the zeolite or impregnated into it.

Prior to use, the zeolite should be dehydrated at least partially. This can be done by heating to a temperature in the range of 400° F. to 1100° F. in air or an inert atmosphere such as nitrogen for 1 to 48 hours. Dehydration can also be performed at lower temperatures merely by using a vacuum, but a longer time is required to obtain a sufficient amount of dehydration.

The upgrading reaction may be conducted by contacting the feedstock with a fixed stationary bed of catalyst, a fixed fluidized bed or with a moving bed. The catalyst may be thereafter regenerated by treating with $H_2$, $CH_4$, $C_3H_8$, benzene, and toluene gases, or burning in air or other oxygen-containing gas.

EXAMPLE

A mixed $C_7$ and $C_9$ feedstock was upgraded under the following conditions:

| | |
|---|---|
| Make up $H_2$ purity, %: | 92 |
| WHSV | 1.5 |
| $H_2$/Feed ratio, mol/mol | 4.0 |
| Reactor Temp. °F. | |
| Inlet | 900 |
| Outlet | 930 |
| Pressure, Psig | |
| Inlet | 485 |
| Outlet | 470 |

The results are summarized and analyzed in Table IV below:

TABLE IV

| FEED, LBS/HR Component | FRESH FEED | $C_9$ AROMATICS RECYCLE | TOLUENE RECYCLE | REACTOR CHARGE | REACTOR EFFLUENT |
|---|---|---|---|---|---|
| $C_2$-$C_5$ | 50 | | | 50 | 2170 |

TABLE IV-continued

| FEED, LBS/HR Component | FRESH FEED | C9 AROMATICS RECYCLE | TOLUENE RECYCLE | REACTOR CHARGE | REACTOR EFFLUENT | | |
|---|---|---|---|---|---|---|---|
| Benzene | 205 | | | 205 | 7400 | | |
| Toluene | 13235 | | 24550 | 37785 | 24550 | | |
| Ethylbenzene | | | | | 150 | | |
| Xylenes | | | | | 11000 | | |
| | | | | | * | | * |
| Propylbenzene | 295 | 20 | | 315 | 295 | 20 | 20 |
| N-nonan | | | | | | | |
| Methylethylbenzene | 2305 | 115 | | 2420 | 2305 | 115 | 110 |
| Trimethylbenzene | 4735 | 4365 | | 9100 | 4735 | 4365 | 2270 |
| Indane | 105 | | | 105 | 105 | | |
| Butylbenzene | 20 | | | 20 | 20 | 250 | 250 |
| TOTAL | 20950 | 4500 | | 50000 | 50000 | | |

*When pseudocumene and mesitylene are produced, the C9 aromatic recycle stream is eliminated and the product yields and distribution are estimated as indicated. Trimethylbenzenes are recovered in which the ratio of psuedocumene to mesitylene is 5 to 1.

What is claimed is:

1. A process for upgrading $C_9$ alkylaromatics, wherein mesitylene and pseudocumene are recovered from a mixture of $C_9$ aromatics including propylbenzene and methylethylbenzene, said process comprising the steps of:
   (a) contacting a $C_9$ alkylaromatic feed stream with a shape-selective crystalline zeolite catalyst having a silica-to-alumina ratio of at least 12 and a constraint index from about 1 to 12 in the presence of hydrogen at a temperature of about 700° F. to 1100° F., a pressure of about 15 to 2000 p.s.i.g., a hydrogen to hydrocarbon mole ratio of 0.5 to 10.0 and a weight hourly space velocity of about 0.5 to 10.0, thereby selectively converting said propylbenzene and methylethylbenzene and forming a product mixture effluent comprising benzene, toluene, $C_8$ alkylbenzenes, $C_9$ alkylbenzenes and $C_{10}$ alkylbenzenes;
   (b) introducing the product mixture to a first distillation zone wherein benzene and toluene are distilled as an overhead fraction and materials heavier than toluene are separated as a first bottoms fraction;
   (c) introducing the first bottoms fraction to a second distillation column wherein xylene is distilled as an overhead fraction and materials heavier than xylene, comprising $C_9$ and $C_{10}$ alkylbenzenes, are separated as a second bottoms fraction;
   (d) introducing the second bottoms fraction to a third distillation column wherein mesitylene is distilled as an overhead fraction and $C_9$ and $C_{10}$ alkylbenzenes are separated as a third bottoms fraction;
   (e) introducing the third bottoms fraction to a fourth distillation column wherein pseudocumene is distilled as an overhead fraction and $C_9$ and $C_{10}$ alkylbenzenes are separated as a fourth bottoms fraction.

2. The process of claim 1 wherein the temperature is between 800° F. to 1000° F. and the pressure is between 50 to 800 p.s.i.g. utilizing a weight hourly space velocity between 1.0 and 5.0.

3. The process of claim 1 wherein the benzene and toluene overhead fraction from the first distillation column is recycled to the upgrading step.

4. The process of claim 1 wherein the $C_9$ alkylaromatic feedstock is coprocessed with roluene or a $C_7$ to $C_9$ mixed alkylaromatic feedstock.

5. The process of claim 1 wherein the $C_9$ alkylaromatic feedstock has an initial boiling point in the range of 230°–280° F., an end boiling point in the range of 350°–425° F., and an API gravity of 35-60.

6. The process of claims 1, 2, 3 or 4 wherein at least a portion of the bottoms product separated from the second distillation column is recycled to the upgrading step.

7. The process of claim 1 wherein the crystalline zeolite is ZSM-5.

8. The process of claim 7 wherein the zeolite contains from about 0.01 to 5.0 weight percent of a hydrogenation component selected from the group consisting of platinum, nickel, molybdenum, cobalt and zinc.

9. The process of claim 1 wherein toluene from step (b) is recycled to step (a) for contact with said catalyst along with said $C_9$ alkylaromatic feed.

10. The process of claim 1 wherein $C_{10}$ bottoms from step (e) are recycled to step (a) for contact with said catalyst along with said $C_9$ alkylaromatic feed.

11. The process of claim 1 wherein said catalyst of step (a) is free of noble metal.

12. The process of claim 1 wherein said temperature of step (a) is from 800° F. to 1000° F.

13. The process of claim 1 wherein said pressure of step (a) is from 150 to 800 p.s.i.g.

14. The process of claim 1 wherein xylenes are produced by transalkylation reactions in step (a).

15. The process of claim 1 wherein xylenes are produced by disproportionation reactions in step (a).

* * * * *